United States Patent [19]

Unger

[11] 4,434,227

[45] Feb. 28, 1984

[54] IMMUNOASSAY FOR CLASS SPECIFIC IMMUNOGLOBULIN ANTIBODIES

[75] Inventor: John T. Unger, Lindenhurst, Ill.

[73] Assignee: Abbott Laboratories, North Chicago, Ill.

[21] Appl. No.: 346,662

[22] Filed: Feb. 8, 1982

[51] Int. Cl.³ .............................................. G01N 33/54
[52] U.S. Cl. ....................................... 435/7; 436/509; 436/513; 436/534; 436/825
[58] Field of Search .................... 435/7; 436/509, 513, 436/518, 524, 525, 526, 527, 528, 529, 530, 531, 532, 533, 534, 535, 825

[56] References Cited

U.S. PATENT DOCUMENTS

| | | | |
|---|---|---|---|
| 4,060,597 | 11/1977 | Sato et al. | 436/509 |
| 4,143,124 | 3/1979 | Masson et al. | 436/513 |
| 4,166,106 | 8/1979 | Sedlacek et al. | 436/805 |
| 4,184,847 | 1/1980 | Hallgren et al. | 436/513 |
| 4,235,869 | 11/1980 | Schwarzberg | 435/7 |
| 4,292,403 | 9/1981 | Duermeyer | 435/7 |
| 4,347,311 | 8/1982 | Schmitz | 436/518 |

OTHER PUBLICATIONS

Vejtorp, "The Interference of IgM Rheumatoid Factor in Enzyme Linked Immunosorbent Assays of Rubella IgM and IgG Antibodies", Journal of Virological Methods 1, (1980), pp. 1-9.

Fundenberg et al., "Basic and Clinical Immunology", 2nd edition, Lange Medical Publications, (1978), pp. 357 and 364-366.

*Primary Examiner*—Robert J. Warden
*Assistant Examiner*—John E. Tarcza
*Attorney, Agent, or Firm*—Steven M. Odre

[57] ABSTRACT

A method for determining an immunoglobulin of the IgX class in a sample where X is either M, A, D or E. Anti-IgG is added to IgG to prevent binding of rheumatoid factor before the sample containing IgX is added to insolubilized IgG.

21 Claims, No Drawings

IMMUNOASSAY FOR CLASS SPECIFIC IMMUNOGLOBULIN ANTIBODIES

BACKGROUND OF THE INVENTION

The immunoglobulin molecule consists of one or more sets of four polypeptide chains, two heavy chains having a molecular weight of about 53,000 daltons and two light chains having a molecular weight of about 22,000 daltons, joined by disulfide bonds.

The immunoglobulins are generally subdivided into five classes: G, M, A, D and E. Immunoglobulins of these classes are generally represented by IgG, IgM, IgA, IgD and IgE, respectively.

Five classes of immunoglobulin ar distinguished by the presence of heavy-chain antigenic determinants, which are designated by the lower case Greek character corresponding to the Roman letters applied to the immunoglobulins:

| IMMUNOGLOBULIN | HEAVY-CHAIN ANTIGENIC DETERMINANT |
|---|---|
| IgG | $\gamma$ (gamma) |
| IgA | $\alpha$ (alpha) |
| IgM | $\mu$ (mu) |
| IgD | $\delta$ (delta) |
| IgE | $\epsilon$ (epsilon) |

There are also subclasses of IgG, IgA, and IgM, based upon other antigenic determinants, which are designated by numerals (e.g., $\gamma 1$, $\alpha 1$, $\mu 1$). Four subclasses for IgG have been recognized, two of IgA, and two of IgM. All subclasses are found in the sera of all normal individuals.

IgG is the most abundant immunoglobulin in the serum of normal humans. It is also found in the tissue fluids, and it can cross the placenta from the material to the fetal circulations. It has antibacterial, antiviral, and antitoxic activities in vivo, and in vitro. It is a late responding antibody.

IgM is characterized by possession of heavy chains with the amino acid sequence that defines the antigenic determinant $\mu$. A distinguishing feature of IgM function is its strong cytolytic and complement-fixing activity, which far exceeds that of IgG. IgM is usually the first antibody to appear in animals or humans following immunization. It is then gradually replaced by IgG.

IgA is the second most abundant immunoglobulin in human serum and is the chief secretory immunoglobulin. It is useful in antibacterial and respiratory viral defense.

IgE is the least abundant immunoglobulin. It has skin sensitizing properties and is responsible for a variety of bronchial, gastrointestinal, skin and other allergic reactions.

Very little is known about the structure and biological function of IgD. IgD antibodies have been found in auto-immine diseases and patients sensitive to cow's milk and patients with systemic lupus erythematosus.

Methods for isolating the above immuniglobulin classes are well-known. Methods for raising antibodies to immunoglobulins are also known and methods for binding immunoglobulins to solid supports are known. Methods for isolating antibodies, labeling antibodies with fluorescent molecules, radioactive molecules or enzymes to permit measuring bound antibody are well-known. There are likewise, indirect methods for measuring bound antibody, such as reacting the bound antibody with a labeled (radioactive, fluorescent, enzyme) antibody specific to the antibody.

The determination of antigen specific immunoglobulins of a peculiar class is of particular clinical significance. U.S. Pat. No. 4,020,151 describes an immunoassay for IgG, IgA, and IgM concentrations in the serum which comprises first reacting a solid support with test sample to absorb IgG, IgA, IgM and then reacting a labeled antibody to IgG, IgA and IgM and measuring the bound antibody. Antigen specific immunoglobulins may also be determined utilizing immunoassay techniques, employing immuno components having binding affinity to the antibody to be determined and/or detected. According to such techniques, an immuno component with binding affinity to the antibody to be determined is coupled to a solid support and another specific immuno component is labeled, for example, with a fluorescent, chromophoric, radioactive group or with an enzyme.

However, one disadvantage associated with such techniques is, that if rheumatoid factor, which may be found in serum, is present in the sample false positive results may be obtained. Rheumatoid factor (RF) generally has affinity for antibodies of the IgG class. RF binds via the constant regions of the heavy chains of the IgG molecule. For example, in an assay for a rubella virus class specific immunoglobulin of IgM class, the rheumatoid factor is itself also an immunoglobulin of the IgM class. Because the rheumatoid factor is usually of the IgM class, it will also be bound by anti-IgM immunoglobulins, thereby, producing false positive results. One method for avoiding such rheumatoid factor interference requires separation of the different immunoglobulin class antibodies prior to analysis. However, the methods for separation of immunoglobulins of different classes and especially of antigen specific immunoglobulins of different classes are generally elaborate and time consuming. Such methods include chromatography, electrophoresis, and density gradient configuration.

U.S. Pat. No. 4,273,756 describes an immunoassay for class specific antibodies, IgG, IgM, IgA, IgE and IgD, which comprises first reacting a solid support on which is coated on antibody for a specific immunoglobulin class is contacted with a sample containing a class specific antibody and then reacting the resulting complex with a labeled antigen and measuring the bound labeled antigen.

U.S. Pat. No. 4,292,403 describes an immunoassay for the determination of an antigen specific immunoglobulin of the class IgM, IgA, IgD, and IgE, which comprises contacting the particular antigen specific immunoglobulin with an insolubilized antibody against the antigen specific immunoglobulin or an antigen binding fragment of this anti-immunoglobulin, then treating the mixture with an antigen for which the immunoglobulin has specific affinity and finally treating the mixture with a labeled antigen binding fragment of an antibody against the antigen and then measuring the labeling fragment. This reference suggests that rheumatoid factor interference is removed.

Voller, et al., *British Journal of Experimental Pathology*, (1975) 56, 338, Gravell, et al., *The Journal of Infectious Disease*, Vol. 136, Supplement (1977), S300, and Cleary, et al., Research Communication in *Chemical Pathology and Pharmacology*, Vol. 19, No. 2, (1978) 281, describe enzyme-linked immunoassays for detecting antibodies to rubella virus.

SUMMARY OF THE INVENTION

The present invention relates to a method for determining an immunoglobulin antibody of an IgX class in a sample, wherein X is selected from the group consisting of M, A, D, and E, said improvement comprising treating the sample with an effective amount of an immunoreagent specific for IgG and sufficient to prevent binding of rheumatoid factor to IgG. In particular, the present invention relates to a method for determining an immunoglobulin antibody of an IgX class in a sample, wherein X is selected from the group consisting of M, A, D, and E, comprising:

(a) treating the sample with an effective amount of anti-IgG;

(b) contacting the treated sample with a class specific antibody reagent comprising an antigen, for which the IgX antibody is specific, coated on a solid support; to form an antigen-IgX complex on the solid support;

(c) removing unbound sample;

(d) treating the antigen-IgX complex with anti-IgX; and (e) determining the anti-IgX bound to the antigen-IgX complex as a measure of the IgX in the sample.

DETAILED DESCRIPTION OF THE INVENTION

The term "immunoreagent" as used herein refers to an antigen, preferably an antibody, for which an immunoglobulin of an IgG class is specific and which complexes IgG in a manner sufficient to prevent binding of rheumatoid factor to the IgG. It is most preferred to employ anti-IgG as the immunoreagent in the methods of the present invention. In addition it is preferred to treat the sample, containing the immunoglobulin antibody IgX of interest, prior to undertaking an immunoassay for the IgX. Various types of immunoassays for IgX may be employed within the scope of the improved method of the present invention, it is preferred to employ an immunoassay procedure wherein an antigen for which the immunoglobulin antibody IgX is specific, is utilized to form an antigen-IgX complex. The antigen-Igx complex thus produced may then be determined using for example, immunoprecipitation, sandwich or competitive assay techniques.

Although the immunoreagent may be employed either before, after or simultaneously with the antigen used to form an anti-IgX complex, it is preferred to employ the immunoreagent prior to treating the sample with the antigen.

As used herein, the term "antigen" refers to biologically active molecules capable of inducing an immunoresponse in either a human or nonhuman species. Illustrative of such antigens include, for example, serum proteins, tissue proteins, antibodies, viral proteins, bacterial lipopolysaccharides, and the like.

According to a preferred embodiment of the present invention, a sample containing immunoglobulin antibody of an IgX class, is treated with an effective amount of anti-IgG in a buffered solution. The resulting mixture is incubated for a sufficient period of time to permit essentially all of the immunoglobulin of IgG class in the sample to complex with the anti-IgG. Following the incubation period, the treated sample is brought in contact with a class specific antibody reagent comprising an antigen specific to the IgX antibody of interest, coated on a solid support. The resulting mixture is incubated for a sufficient period of time to allow formation of an antigen-IgX complex on the solid support. The antigen-IgX complex on the solid support is washed with water to remove unbound sample and then treated with anti-IgX. The resulting mixture is then incubated for a period of time sufficient to allow the formation of an antigen-IgX-anti-IgX complex on the solid support. The antigen-IgX-anti-IgX complex coated on the solid support is washed with water and the amount of anti-IgX bound to the antigen-IgX complex is determined as a measure of the particular IgX in the sample.

In accordance with the present invention the immunoglobulins of IgX class that may be determined by the methods of the present invention include IgM, IgA, IgE and IgD.

Solid support refers to an insoluble polymeric material sorptive for the antigen. Known materials of this type include hydrocarbon polymers such as polystyrene, polyethylene, polypropylene, polybutylene, butyl rubber and other synthetic rubbers. Other suitable organic polymers include silastic rubber, polyesters, polyamides, cellulose and cellulosic derivatives, acrylates, methacrylates, and vinyl polymers such as vinyl chloride, and polyvinylchloride. Copolymers such as graft copolymers of polystyrene are also useful. In addition to the foregoing materials, the solid support surface may comprise silica gel, silicone wafers, glass insoluble protein metals and the solid support may be in the form of beads, tubes, strips, disks, microtetration plates and the like.

The antigens employed in the class specific antibody reagent include antigens, capable to binding a class specific antibodies IgG, IgM, IgA, IgD and IgE, and may be obtained from either human or nonhuman sources. Tissue culture techniques may be employed to propagate the antigen. The antigens are coated on a solid support and preferably are coated on a polystyrene bead. The antigens may be coated on the solid support using various techniques. For ease of operation, it is preferred that the antigen be coated on the solid support by placing the solid support to be coated in a solution containing the antigen for a period of time, then washing and air-drying the solid support.

The term "anti-IgG" refers to an antibody specific for human IgG, and is raised in a nonhuman species such as rabbit, goat, horse, sheep, guinea pig, etc. The addition of an effective amount of anti-IgG to the sample binds any IgG immunoglobulins present in the samples. The binding of the IgG by anti-IgG prior to contacting the sample with a class specific antibody reagent complexes the rheumatoid factor binding sites on the IgG thereby preventing rheumatoid factors from binding to the IgG. Therefore, only IgM, IgA, IgD or IgE immunoglobulins in the sample as well as the IgG-anti-IgG complex may bind to the antigen on the solid support. The treated sample and class specific antibody reagent are incubated and then washed with water to remove unbound immunoglobulins in the test sample. Thus, class specific immunoglobulins, IgX, including those present in the serum because of infection and which contain antibodies to the infecting agent will form an antigen-IgX complex and adhere to the solid support. In addition, the IgG-anti-IgG complex previously formed, may form an antigen-IgG-anti-IgG complex and thereby adhere to the solid support.

The antigen-IgX complex is reacted with a known anti-IgX to form an antigen-IgX-anti-IgX complex on solid support. The anti-IgX bound to the antigen-IgX complex is determined as a measure of the IgX in the sample. The anti-IgX may be directly labeled by conventional fluorescent dyes, enzymes or radioactive labels to permit determination of the amount bound, or it may be indirectly labeled by further reaction, for example, with an antibody specific for the anti-IgX, and is labeled with fluorescent dyes, enzymes or radioactive labels by conventional methods. The anti-IgX employed is generally an IgG immunoglobulin specific to the IgX to be determined and raised in a nonhuman species.

It is preferred to employ direct enzyme labeling of the anti-IgX. Examples of enzymes include catalase, peroxidase, urease, glucose oxidase, phosphatase, and the like. If direct labeling of the anti-IgX is employed, following the formation of the antigen-IgX-anti-IgX* complex, wherein anti-IgX* refers to labeled anti-IgX, an enzyme substrate is added to the liquid and/or solid phase of the reaction mixture and an enzymatic determination if performed by conventional techniques such as colorimetrically, fluorimetrically or spectrophotometrically to measure the bound labeled anti-IgX. In the case of indirect labeling, that is, the anti-IgX is unlabeled, the antigen-IgX-anti-IgX complex is washed to remove unbound anti-IgX and subsequently reacted with a labeled antibody to the anti-IgX and the bound labeled antibody is then measured.

In addition the present invention provides a method for determining IgG in a sample containing rheumatoid factor. It has been found that the antigen-IgG, anti-IgG complex that was formed on the solid support in the above-described procedure may be subsequently treated with a labeled anti-IgG* specific for the anti-IgG bound on the anti-IgG-anti-IgG complex and the bound labeled anti-IgG* may be then determined as a measure of IgG present in the sample.

As used herein, the term "an effective amount of anti-IgG" refers to a quantity of anti-IgG sufficient to bind all the IgG in the sample to be assayed, thereby preventing any binding of IgG and RF.

The following examples illustrate the present invention and are not intended to limit it in spirit or scope.

EXAMPLE 1

Preparation Of Rubella Virus Antigen Coated Beads

Rubella virus, Gilchrest strain, was produced in BHK 21 Clone 13 cells in a nutrient medium. The viral antigens were isolated by ultracentrifugation of the medium. The suspension was diluted 1:50 with 0.1 M Tris at a pH of 8.6. The diluted solution was used to coat 6 mm polystyrene beads overnight at room temperature, and each set of beads was washed and air dried.

Determination of IgM Antibodies Against Rubella Virus

1. A serum sample and negative, high positive and three low positive controls were diluted 1:21 in a solution containing 0.1 M Tris, 0.5 M sodium chloride, 0.01% Tween 20 and 1 mg/ml bovine serum albumin at a pH of 7.6.

2. A 20 µl aliquot of the diluted sample and each diluted control was added to appropriate wells of a reaction tray.

3. Into each well containing diluted sample of control was added 200 µl of a mixture containing 1.5% goat antihuman IgG, 53.5% calf serum, 0.01% Tween 20, and a 44.99% mixture of 0.1 M Tris and 0.5 M sodium chloride adjusted to yield final pH of 7.6.

4. The reaction trays were covered and incubated for sixty minutes at 45° C.

5. Following the incubation period, a bead coated with rubella virus antigen was added to each well containing a sample or control and the reaction trays were again covered and incubated for ninety minutes at 45° C.

6. Following this second incubation, unbound sample or control was removed from the wells and the beads were washed twice with water.

7. To the wells containing the washed beads was added 200 µl of a solution containing from 0.05-3 µg/ml of goat antihuman IgM covalently linked to horseradish peroxidase, 10% bovine serum in 0.1 M Tris and 0.15 M sodium chloride.

8. The reaction trays were covered and incubated for ninety minutes at 45° C.

9. Following the incubation, unbound goat antihuman IgM-horseradish peroxidase was removed and the beads were washed twice with 5 ml of water.

10. The beads from the wells originally containing the samples and controls were transferred to assay tubes to which was then added 300 µl of a freshly prepared substrate solution containing approximately 27 mg of o-phenylene diamine.2HCl in 5 ml of citrate-phosphate buffer at a pH of 5.5. The tubes were then incubated for 30 minutes at room temperature.

11. Following the incubation, 2 ml of 1 N hydrochloric acid was added to each tube and the absorbance of the resulting sample and control solutions were read on a spectrophotometer at 492 nm.

12. An absorbance value for the sample 1.09 times greater than or 0.91 times less than the average of the three low controls was taken as the boundaries between positive and negative results respectively. An absorbance value between 1.09 and 0.91 times the average of the three low controls suspects rubella infection but does not confirm it.

The sensitivity of the assay described in Example I is determined by the level of the low positive control that is employed. In the above, a low positive control having a value for IgM that coincides with the value for the limit of sensitivity described in the hemagglutination inhibition sucrose density gradient test procedure described by Palmer, D. F., et al., Rubella Hemagglutination-Inhibition Tests, Immunology Series, No. 2 (revised) Center For Disease Control, Atlanta, 1977 was employed.

EXAMPLE 2

Various specimens obtained from individuals suffering viral infections other than rubella, from multiple myeloma patients and specimens positive for anti-nuclear antibody and/or rheumatoid factor, were assayed in accordance with the methods of the present invention. No false positive results due to viral infections, multiple myeloma, anti-nuclear antibody or rheumatoid factor were observed.

As noted by the above-described procedures, the methods of the present invention provides an immunoassay for the determination of class specific immunoglobulins in samples containing rheumatoid factor. The invention further provides an immunoassay procedure for the determination of class specific immunoglobulins in samples containing rheumatoid factor which such procedures do not require the separation of the various immunoglobulins or the removal of rheumatoid factor from the sample prior to binding of the immunoglobulins to the class specific antibody reagent.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A method for determining an immunoglobulin antibody of an IgX class in a sample, wherein X is selected from the group consisting of M, A, D and E, comprising:
   (a) treating the sample with an effective amount of anti-IgG;
   (b) contacting the treated sample with a class specific antibody reagent comprising an antigen, for which the immunoglobulin antibody IgX is specific, coated on a solid support; to form an antigen-IgX complex on the solid support;
   (c) removing unbound sample;
   (d) treating the antigen-IgX complex with anti-IgX; and
   (e) determining the anti-IgX bound to the antigen-IgX complex as a measure of IgX in the sample.

2. A method according to claim 1 wherein the amount of anti-IgG of step (a) is immunochemically greater than the amount of IgG in the sample.

3. A method according to claim 2 wherein the anti-IgX is labeled with an enzyme.

4. A method according to claim 3 wherein unbound labeled anti-IgX is removed prior to determining the labeled anti-IgX bound to the antigen-IgX complex.

5. A method according to claim 1 or 4 wherein IgX is an IgM antibody against rubella virus.

6. A method according to claim 1 wherein step (c) is preformed by aspiration of the unbound sample and washing of the solid support with water.

7. A method for determining an immunoglobulin antibody of an IgX class in a sample, wherein X is selected from the group consisting of M, A, D and E, comprising:
   (a) treating the sample with an effective amount of anti-IgG;
   (b) contacting the treated sample with a class specific antibody reagent comprising an antigen, for which the immunoglobulin antibody IgX is specific, coated on a solid support; to form an antigen-IgX complex on the solid support;
   (c) removing unbound sample;
   (d) treating the antigen-IgX complex with labeled anti-IgX;
   (e) removing unbound labeled anti-IgX; and
   (f) determining the labeled anti-IgX bound to the antigen-IgX complex as a measure of IgX in the sample.

8. A method according to claim 7 wherein the labeled anti-IgX is labeled with an enzyme.

9. A method according to claim 8 wherein IgX is an IgM antibody against rubella virus.

10. A method according to claim 7 wherein steps (c) and (e) are preformed by aspiration of the unbound sample and labeled anti-IgX respectively and washing of the solid support.

11. A method for determining an immunoglobulin antibody of an IgX class in a sample, wherein X is selected from the group consisting of M, A, D and E, comprising:
   (a) treating the sample with an effective amount of anti-IgG;
   (b) contacting the treated sample with a class specific antibody reagent comprising an antigen, for which the immunoglobulin antibody IgX is specific, coated on a solid support; to form an antigen-IgX complex on the solid support;
   (c) removing unbound sample;
   (d) treating the antigen-IgX complex with anti-IgX;
   (e) removing unbound anti-IgX;
   (f) treating the antigen-IgX-anti-IgX with labeled antibody to anti-IgX;
   (g) removing unbound labeled antibody to the anti-IgX; and
   (h) determining the labeled antibody bound to the antigen-IgX-anti-Igx complex as a measure of IgX in the sample.

12. A method according to claim 11 wherein the amount of anti-IgG of step (a) is immunochemically greater than the amount of IgG in the sample.

13. A method according to claim 11 wherein the labeled antibody to anti-IgX is labeled with an enzyme.

14. A method according to claim 13 wherein IgX is an IgM antibody against rubella virus.

15. A method according to claim 11 wherein steps (c), (e) and (g) are preformed by aspiration of the unbound sample, unbound labeled anti-IgX and unbound labeled antibody to anti-IgX repsectively and washing of the solid support.

16. A method for determining an immunoglobulin antibody of an IgG class in a sample comprising:
   (a) treating the sample with an effective amount of anti-IgG;
   (b) contacting the treated sample with a class specific antibody reagent comprising an antigen for which the immunoglobulin antibody IgG is specific, coated on a solid support; to form an antigen-IgG-anti-IgG complex on the solid support;
   (c) removing unbound sample;
   (d) treating the antigen-IgG-anti-IgG complex with antibody to anti-IgG; and
   (e) determining the antibody to anti-IgG bound to the antigen-IgG-anti-IgG complex as a measure of IgG in the sample.

17. A method according to claim 16 wherein the amount of anti-IgG of step (a) is immunochemically greater than the amount of IgG in the sample.

18. A method according to claim 16 wherein the antibody to anti-IgG is labeled with an enzyme.

19. A method according to claim 18 wherein step (e) unbound labeled antibody to IgG is removed prior to determinating the amount of bound antibody to anti-IgG in the sample.

20. A method according to claim 19 wherein the unbound labeled antibody to IgG is removed by aspiration and washing of the solid support.

21. A method according to claim 16 wherein step (c) is preformed by aspiration of the unbound sample and washing of the bead.

* * * * *